United States Patent
Kim et al.

(10) Patent No.: US 10,182,756 B2
(45) Date of Patent: Jan. 22, 2019

(54) MOBILE TERMINAL AND CONTROL METHOD THEREFOR

(71) Applicant: LG ELECTRONICS INC., Seoul (KR)

(72) Inventors: Sungyup Kim, Seoul (KR); Youngkyung Jung, Seoul (KR); Jihyun Kim, Seoul (KR); Sungjae Chung, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/514,482

(22) PCT Filed: Oct. 2, 2014

(86) PCT No.: PCT/KR2014/009352
§ 371 (c)(1),
(2) Date: Mar. 24, 2017

(87) PCT Pub. No.: WO2016/052788
PCT Pub. Date: Apr. 7, 2016

(65) Prior Publication Data
US 2017/0273612 A1    Sep. 28, 2017

(51) Int. Cl.
*G08B 23/00* (2006.01)
*A61B 5/16* (2006.01)
(Continued)

(52) U.S. Cl.
CPC ............ *A61B 5/165* (2013.01); *A61B 5/0002* (2013.01); *A61B 5/11* (2013.01); *A61B 5/486* (2013.01);
(Continued)

(58) Field of Classification Search
CPC ................................... A61B 1/00; G06F 1/00
See application file for complete search history.

(56) References Cited

U.S. PATENT DOCUMENTS

| | | | |
|---|---|---|---|
| 2008/0208015 A1 | 8/2008 | Morris et al. | |
| 2010/0045463 A1* | 2/2010 | Bradley | A01K 11/008 340/573.1 |
| 2011/0257542 A1* | 10/2011 | Russell | A61B 5/0205 600/500 |

FOREIGN PATENT DOCUMENTS

| | | |
|---|---|---|
| EP | 2540220 | 1/2013 |
| JP | 2009217378 | 9/2009 |

(Continued)

OTHER PUBLICATIONS

PCT International Application No. PCT/KR2014/009352, Written Opinion of the International Searching Authority dated Jun. 19, 2015, 4 pages.

(Continued)

*Primary Examiner* — Shirley Lu
(74) *Attorney, Agent, or Firm* — Lee, Hong, Degerman, Kang & Waimey

(57) ABSTRACT

A mobile terminal and a control method therefor are disclosed. An embodiment of the present invention comprises: a detection unit for monitoring a stress index on the basis of a user's biometric information and detecting a first interval where the rate of change at which an increased stress index decreases exceeds a reference range; a storage unit for storing context information corresponding to the detected first interval; and a control unit for, when a second interval where the rate of change at which the increased stress index decreases is less than the reference range occurs, generating stress relief information using the stored context information and outputting the generated stress relief information.

18 Claims, 16 Drawing Sheets

(51) Int. Cl.
*G06Q 50/22* (2018.01)
*H04W 4/02* (2018.01)
*H04W 88/02* (2009.01)
*A61B 5/00* (2006.01)
*A61B 5/11* (2006.01)
*A61M 21/02* (2006.01)
*G08B 21/04* (2006.01)
*G06Q 50/00* (2012.01)
*A61M 21/00* (2006.01)

(52) U.S. Cl.
CPC .......... *A61B 5/4866* (2013.01); *A61B 5/6898* (2013.01); *A61B 5/7435* (2013.01); *A61M 21/02* (2013.01); *G06Q 50/01* (2013.01); *G06Q 50/22* (2013.01); *G08B 21/0453* (2013.01); *H04W 4/02* (2013.01); *H04W 88/02* (2013.01); *A61M 2021/005* (2013.01); *A61M 2021/0027* (2013.01)

(56) References Cited

FOREIGN PATENT DOCUMENTS

| | | |
|---|---|---|
| JP | 2010207553 | 9/2010 |
| KR | 10-2009-0052786 | 5/2009 |
| KR | 20100008875 | 1/2010 |
| KR | 10-2012-0010398 | 2/2012 |

OTHER PUBLICATIONS

European Patent Office Application Serial No. 14903366.4, Search Report dated Jun. 26, 2018, 8 pages.

\* cited by examiner

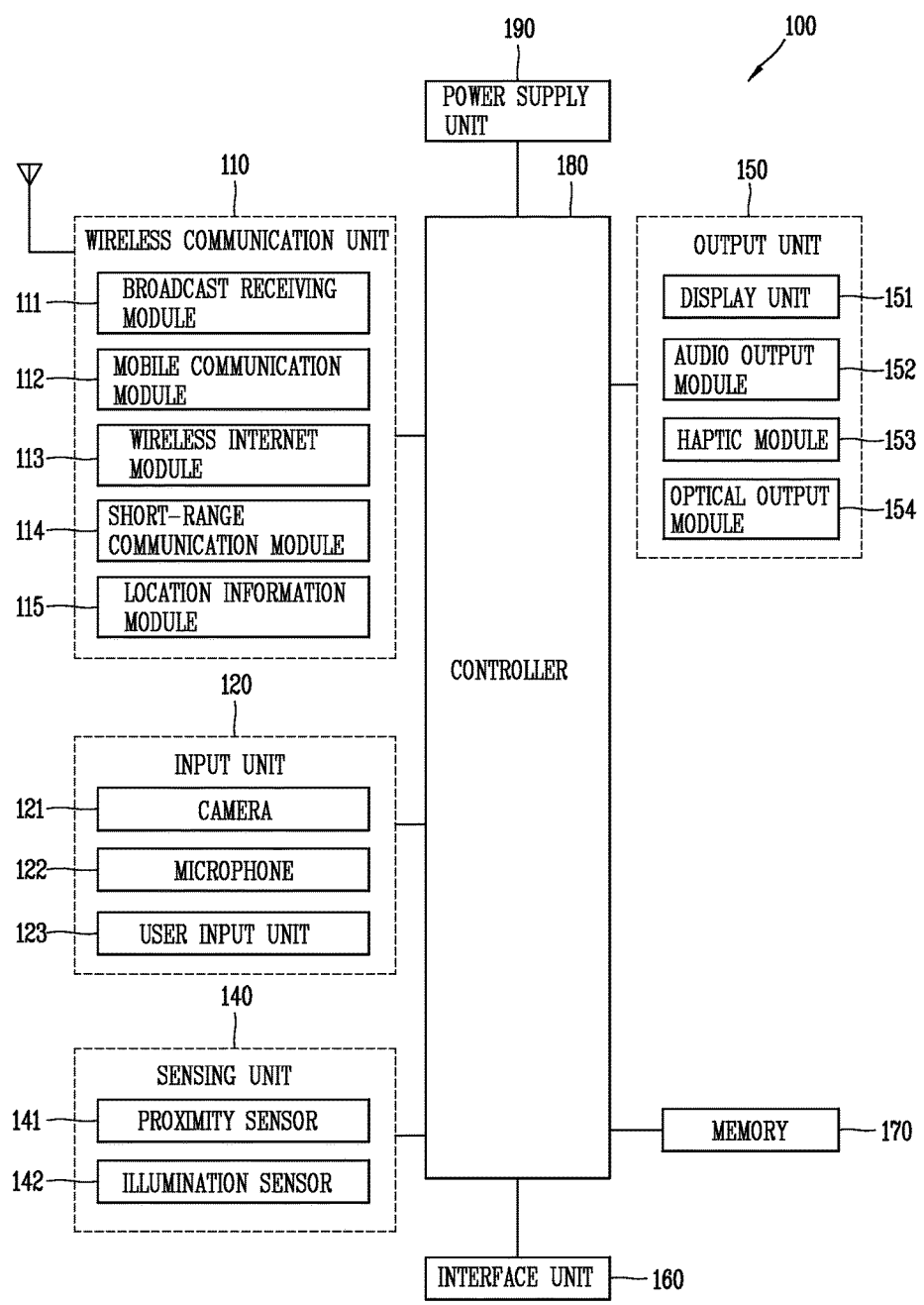

(a)           (b)

(a)            (b)

MOBILE TERMINAL AND CONTROL METHOD THEREFOR

CROSS-REFERENCE TO RELATED APPLICATIONS

This application is the National Stage filing under 35 U.S.C. 371 of International Application No. PCT/KR2014/009352, filed on Oct. 2, 2014, the contents of which are all hereby incorporated by reference herein in their entirety.

TECHNICAL FIELD

The present invention relates to a mobile terminal capable of calculating a stress index based on a user's biometric information, and a method for controlling the same.

BACKGROUND ART

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions may include data and voice communications, capturing images and video through a camera, recording audio, playing music files through a speaker system, and displaying images and video on a display unit. Some mobile terminals additionally provide functions such as playing an electronic game, or executing a function of multimedia players. Especially, recent mobile terminals may receive multicast signal for providing visual content such as broadcasts, videos, or television programs.

As it becomes multifunctional, a mobile terminal can be allowed to capture still images or moving images, play music or video files, play games, receive broadcast and the like, so as to be implemented as an integrated multimedia player.

Various attempts have been made to implement complicated functions in such a multimedia device by means of hardware or software.

In a case where such a mobile terminal is mounted to various positions on a user's body according to a usage purpose or intention of the user, a movement or a biometric signal of the user may be sensed, and various functions may be performed. For instance, a user's stress index may be calculated based on detected biometric information, and stress of the user may be controlled.

DISCLOSURE OF THE INVENTION

Therefore, an object of the present invention is to provide a mobile terminal capable of providing a service specialized for a user in order to efficiently reduce stress when a calculated stress index is high, and a method for controlling the same.

Another object of the present invention is to provide a mobile terminal capable of rapidly relieving stress by providing context information corresponding to a case where a stress index has been efficiently decreased, and a method for controlling the same.

To achieve these and other advantages and in accordance with the purpose of the present invention, as embodied and broadly described herein, there is provided a mobile terminal, including: a detection unit configured to monitor a stress index based on a user's biometric information, and to detect a first section where a decrease rate of the increased stress index exceeds a reference range; a memory configured to store therein context information corresponding to the detected first section; and a controller configured to generate stress relief information based on the stored context information when a second section where a decrease rate of the increased stress index is less than the reference range occurs, and configured to output the generated stress relief information.

In an embodiment, the controller may ignore context information collected at a section where a decrease rate of the increased stress index is less than the reference range.

In an embodiment, a starting point of each of the first and second sections may be a time point when the increased stress index starts to be decreased, and an ending point of each of the first and second sections may be a time point when the decreased stress index reaches a preset minimum value.

In an embodiment, the context information may be related to at least one of a position of the mobile terminal, a user's state information, a user's motion information, and surrounding environment information, at the first section.

In an embodiment, the mobile terminal may further comprises a display unit configured to output video information. And the controller may output notification information at a time point when the increased stress index exceeds a reference value as a monitoring result, and may output the generated stress relief information to the display unit, in response to lapse of a reference time after the notification information is output.

In an embodiment, the stress relief information may be at least one of a message which guides a stress index decreasing situation corresponding to the stored context information, an image, and a graphic change.

In an embodiment, the stress relief information may be output to a pop-up window including selection icons to select for information reception and non-reception. And in response to an input to the selection icon, the controller may measure a time taken for the increased stress index to be relieved, and may record the measured time together with the stored context information.

In an embodiment, if a section where a decrease rate of the increased stress index is larger than that in the first section is detected by the detection unit, the controller may update the context information stored in the memory.

In an embodiment, the context information corresponding to the first section may be stored in plurality by time. And when the second section occurs, the controller may generate stress relief information by preferentially extracting context information corresponding to an occurrence time point of the second section.

In an embodiment, when the second section occurs, the controller may generate stress relief information by preferentially extracting preferentially extracting context information having a large decrease rate of the stress index, among the stored context information.

In an embodiment, the detection unit may further detect a third section where the stress index is less than a predetermined minimum value. And the memory may further store therein second context information corresponding to the detected third section.

In an embodiment, if the stress index does not reach the predetermined minimum value within a preset time after outputting the stress relief information, the controller may generate second stress relief information based on the stored second context information, and may output the second stress relief information.

In an embodiment, the mobile terminal may further comprises a display unit configured to display the stress relief information. The memory may further store therein time information corresponding to the first section. And if an input to select a reference time is received on the display unit, the controller may generate a stress relief pattern, based on a plurality of context information accumulated for a reference time corresponding to the input, and may output a graphic object indicating the generated stress relief pattern, to the display unit.

In an embodiment, the stress relief pattern may be obtained by grouping the same or similar context information detected for the reference time and corresponding to the first section. And the graphic object may be a graph showing accumulated information of the same or similar context information, on the generated stress relief pattern.

In an embodiment, the mobile terminal may further comprise a position information unit configured to obtain position information of the mobile terminal. And when the second section occurs, the controller may generate stress relief information by correlating the stored context information with the obtained position information.

In an embodiment, the mobile terminal may further comprises a wireless communication unit configured to receive biometric information by connecting to an external device. And the detection unit may monitor the stress index based on the received biometric information.

In an embodiment, when the second section occurs, the controller may transmit a notification signal indicating a delayed state of a decrease of the stress index, to the external device, through the wireless communication unit. And in response to an input applied from the external device which has received the notification signal, the controller may control the wireless communication unit such that stress relief information generated based on the stored context information may be output from the external device.

To achieve these and other advantages and in accordance with the purpose of the present invention, as embodied and broadly described herein, there is also provided a method for controlling a mobile terminal, the method including: monitoring a stress index based on a user's biometric information; detecting a first section where a decrease rate of the increased stress index exceeds a reference range; storing context information corresponding to the detected first section; and generating stress relief information based on the stored context information when a second section where a decrease rate of the increased stress index is less than the reference range occurs; and outputting the generated stress relief information.

In an embodiment, context information, collected at a section where a decrease rate of the increased stress index is less than the reference range, may be ignored.

In an embodiment, the method may further include: detecting a third section where the stress index is less than a predetermined minimum value; storing second context information corresponding to the detected third section; and if the stress index does not reach the predetermined minimum value within a preset time after outputting the stress relief information, outputting second stress relief information generated based on the stored second context information.

Advantageous Effects

In the mobile terminal and the method for controlling the same according to the present invention, only context information generated at a section where a stress index has been efficiently decreased based on a user's biometric information, is collected to be provided to a time point when a decrease of the stress index is delayed. This may allow stress to be reduced more efficiently, and may provide a service specific to a user.

Further, since context information generated at a section where a stress index has been efficiently decreased is accumulated, a stress relief pattern suitable for a user may be displayed. Further, information related to a current time and/or a user's current position is provided to induce a situation corresponding to the stress relief pattern. This may allow the user to manage stress more actively and enhance user's convenience.

BRIEF DESCRIPTION OF THE DRAWINGS

FIG. 1 is a block diagram illustrating a mobile terminal according to the present invention;

MODES FOR CARRYING OUT THE PREFERRED EMBODIMENTS

Figure 2A:
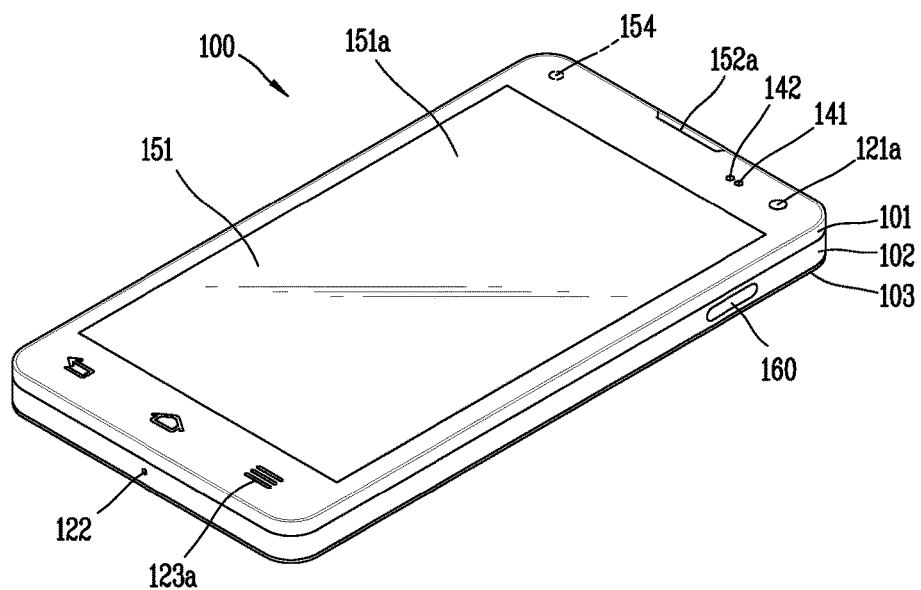
FIGS. 2A and 2B are conceptual views of a mobile terminal according to the present invention, which are viewed from different directions.

Description will now be given in detail according to exemplary embodiments disclosed herein, with reference to the accompanying drawings. For the sake of brief description with reference to the drawings, the same or equivalent components may be provided with the same or similar reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context.

Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart glasses), head mounted displays (HMDs), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and a digital signage.

FIG. 1 is a block diagram of a mobile terminal in accordance with the present disclosure.

The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components of FIG. 1 is not a requirement, and that greater or fewer components may alternatively be implemented.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks.

To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1, the sensing unit 140 is shown having a proximity sensor 141 and an illumination sensor 142. If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few.

The output unit 150 is typically configured to output various types of information, such as audio, video, tactile output, and the like. The output unit 150 is shown having a display unit 151, an audio output module 152, a haptic module 153, and an optical output module 154. The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output by the various components depicted in FIG. 1, or activating application programs stored in the memory 170. As one example, the controller 180 controls some or all of the components illustrated in FIGS. 1A-1C according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

At least some of the above components may operate in a cooperating manner, so as to implement an operation or a control method of the mobile terminal according to various embodiments to be explained later. The operation or the control method of the mobile terminal may be implemented on the image information projection device by driving at least one application program stored in the memory 170.

Referring still to FIG. 1, various components depicted in this figure will now be described in more detail, before explaining various embodiments of the mobile terminal 100.

Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), Wideband CDMA (WCDMA), High Speed Downlink Packet access (HSDPA), Long Term Evolution (LTE), and the like).

Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA(High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, GSM, CDMA, WCDMA, LTE and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some embodiments, another mobile terminal (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal. As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 120. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The controller 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and causes output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

In some embodiments, the controller 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the mobile terminal. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

In some embodiments, the display unit 151 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example. The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

Figure 2B:
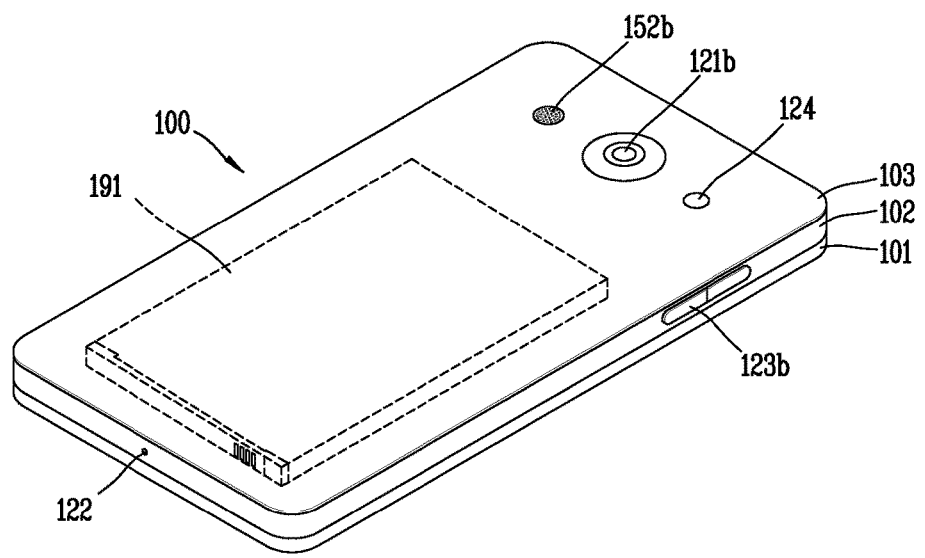

FIGS. 2A and 2B are conceptual views of a mobile terminal according to the present invention, which are viewed from different directions.

Referring now to FIGS. 2A and 2B, the mobile terminal 100 is described with reference to a bar-type terminal body. However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (for example, bar-type, watch-type, glasses-type, and the like). However, such teachings with regard to a particular type of mobile terminal will generally apply to other types of mobile terminals as well.

The terminal body may be understood as at least one integrated assembly of the mobile terminal 100.

The mobile terminal 100 will generally include a case (for example, frame, housing, cover, and the like) forming the appearance of the terminal. In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display unit 151 is shown located on the front side of the terminal body to output information. As illustrated, a window 151a of the display unit 151 may be mounted to the front case 101 to form the front surface of the terminal body together with the front case 101.

In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121b or an audio output module 152b.

The cases 101, 102, 103 may be formed by injection-molding synthetic resin or may be formed of a metal, for example, stainless steel (STS), aluminum (Al), titanium (Ti), or the like.

As an alternative to the example in which the plurality of cases form an inner space for accommodating components, the mobile terminal 100 may be configured such that one case forms the inner space. In this example, a mobile terminal 100 having a uni-body is formed in such a manner that synthetic resin or metal extends from a side surface to a rear surface.

If desired, the mobile terminal 100 may include a waterproofing unit (not shown) for preventing introduction of water into the terminal body. For example, the waterproofing unit may include a waterproofing member which is located between the window 151a and the front case 101, between the front case 101 and the rear case 102, or between the rear case 102 and the rear cover 103, to hermetically seal an inner space when those cases are coupled.

The mobile terminal 100 may be provided with the display unit 151, the first and second audio output modules 152a, 152b, the proximity sensor 141, the illumination sensor 142, the optical output module 154, the first and second cameras 121a, 121b, the first and second manipulation units 123a, 123b, the microphone 122, the interface unit 160, etc.

Hereinafter, as shown in FIGS. 2A and 2B, the mobile terminal 100 will be explained in an assumption that the display unit 151, the first audio output module 152a, the proximity sensor 141, the illumination sensor 142, the optical output module 154, the first camera 121a, and the first manipulation unit 123a are disposed on a front surface of the terminal body, the microphone 122 and the interface unit 160 are disposed on a side surface of the terminal body, and the second audio output module 152b and the second camera 121b are disposed on a rear surface of the terminal body.

However, it is to be understood that alternative arrangements are possible and within the teachings of the instant disclosure. Some components may be omitted or rearranged. For example, the first manipulation unit 123a may be located on another surface of the terminal body, and the second audio output module 152b may be located on the side surface of the terminal body.

The display unit 151 outputs information processed in the mobile terminal 100. The display unit 151 may be implemented using one or more suitable display devices. Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display unit 151 may be implemented using two display devices, which can implement the same or different display technology. For instance, a plurality of the display units 151 may be arranged on one side, either spaced apart from each other, or these devices may be integrated, or these devices may be arranged on different surfaces.

The display unit 151 may also include a touch sensor which senses a touch input received at the display unit. When a touch is input to the display unit 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151a and a display on a rear surface of the window 151a, or a metal wire which is patterned directly on the rear surface of the window 151a. Alternatively, the touch sensor may be integrally formed with the display. For example, the touch sensor may be disposed on a substrate of the display or within the display.

The display unit 151 may also form a touch screen together with the touch sensor. Here, the touch screen may serve as the user input unit 123 (see FIG. 1). Therefore, the touch screen may replace at least some of the functions of the first manipulation unit 123a.

The first audio output module 152a may be implemented in the form of a speaker to output voice audio, alarm sounds, multimedia audio reproduction, and the like.

The window 151a of the display unit 151 will typically include an aperture to permit audio generated by the first audio output module 152a to pass. One alternative is to allow audio to be released along an assembly gap between the structural bodies (for example, a gap between the window 151a and the front case 101). In this case, a hole independently formed to output audio sounds may not be seen or is otherwise hidden in terms of appearance, thereby further simplifying the appearance and manufacturing of the mobile terminal 100.

The optical output module 154 can be configured to output light for indicating an event generation. Examples of such events include a message reception, a call signal reception, a missed call, an alarm, a schedule notice, an email reception, information reception through an application, and the like. When a user has checked a generated event, the controller can control the optical output unit 154 to stop the light output.

The first camera 121a can process image frames such as still or moving images obtained by the image sensor in a capture mode or a video call mode. The processed image frames can then be displayed on the display unit 151 or stored in the memory 170.

The first and second manipulation units 123a and 123b are examples of the user input unit 123, which may be manipulated by a user to provide input to the mobile terminal 100. The first and second manipulation units 123a and 123b may also be commonly referred to as a manipulating portion, and may employ any tactile method that allows the user to perform manipulation such as touch, push, scroll, or the like. The first and second manipulation units 123a and 123b may also employ any non-tactile method that allows the user to perform manipulation such as proximity touch, hovering, or the like.

In the drawings, the first manipulation unit 123a is illustrated as a touch key, but possible alternatives include a mechanical key, a push key, a touch key, and combinations thereof.

Input received at the first and second manipulation units 123a and 123b may be used in various ways. For example, the first manipulation unit 123a may be used by the user to provide an input to a menu, home key, cancel, search, or the like, and the second manipulation unit 123b may be used by the user to provide an input to control a volume level being output from the first or second audio output modules 152a or 152b, to switch to a touch recognition mode of the display unit 151, or the like.

As another example of the user input unit 123, a rear input unit (not shown) may be located on the rear surface of the terminal body. The rear input unit can be manipulated by a user to provide input to the mobile terminal 100. The input may be used in a variety of different ways. For example, the rear input unit may be used by the user to provide an input for power on/off, start, end, scroll, control volume level being output from the first or second audio output modules 152a or 152b, switch to a touch recognition mode of the display unit 151, and the like. The rear input unit may be configured to permit touch input, a push input, or combinations thereof.

The rear input unit may be located to overlap the display unit 151 of the front side in a thickness direction of the terminal body. As one example, the rear input unit may be located on an upper end portion of the rear side of the terminal body such that a user can easily manipulate it using a forefinger when the user grabs the terminal body with one hand. Alternatively, the rear input unit can be positioned at most any location of the rear side of the terminal body.

Embodiments that include the rear input unit may implement some or all of the functionality of the first manipulation unit 123a in the rear input unit. As such, in situations where the first manipulation unit 123a is omitted from the front side, the display unit 151 can have a larger screen.

As a further alternative, the mobile terminal 100 may include a finger scan sensor which scans a user's fingerprint. The controller 180 can then use fingerprint information sensed by the finger scan sensor as part of an authentication procedure. The finger scan sensor may also be installed in the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds.

The interface unit 160 may serve as a path allowing the mobile terminal 100 to interface with external devices. For example, the interface unit 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121b is shown located at the rear side of the terminal body and includes an image capturing direction that is substantially opposite to the image capturing direction of the first camera unit 121a. If desired, second camera 121a may alternatively be located at other locations, or made to be moveable, in order to have a different image capturing direction from that which is shown.

The second camera 121b can include a plurality of lenses arranged along at least one line. The plurality of lenses may also be arranged in a matrix configuration. The cameras may be referred to as an "array camera." When the second camera 121b is implemented as an array camera, images may be captured in various manners using the plurality of lenses and images with better qualities.

A flash 124 is shown adjacent to the second camera 121b. When an image of a subject is captured with the camera 121b, the flash 124 may illuminate the subject.

The second audio output module 152b can be located on the terminal body. The second audio output module 152b may implement stereophonic sound functions in conjunction with the first audio output module 152a, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 (refer to FIG. 1) may be retractable into the terminal body. Alternatively, an antenna may be formed using a film attached to an inner surface of the rear cover 103, or a case that includes a conductive material.

A power supply unit 190 (refer to FIG. 1) for supplying power to the mobile terminal 100 may include a battery 191, which is mounted in the terminal body or detachably coupled to an outside of the terminal body.

The battery 191 may receive power via a power source cable connected to the interface unit 160. Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191, and to protect the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display unit 151 to extend the function of the mobile terminal 100. Another example of the accessory is a touch pen for assisting or extending a touch input to a touch screen.

Figure 3A:
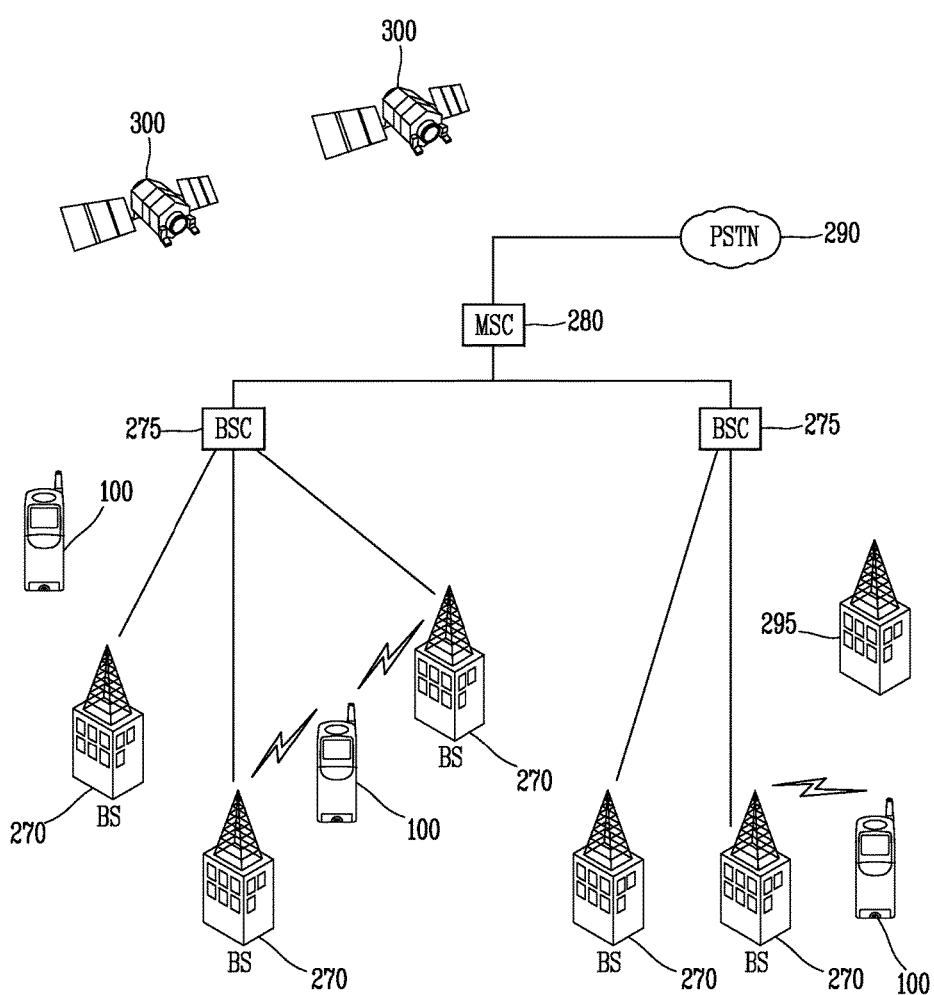
FIGS. 3A and 3B are views for explaining a system where a mobile terminal according to the present invention can be operated.

Hereinafter, a communication system where the mobile terminal 100 according to the present invention can be operated will be explained with reference to FIG. 3A.

A communication system which is operable with the variously described mobile terminals will now be described in more detail. Such a communication system may be configured to utilize any of a variety of different air interfaces and/or physical layers. Examples of such air interfaces utilized by the communication system include Frequency Division Multiple Access (FDMA), Time Division Multiple Access (TDMA), Code Division Multiple Access (CDMA), Universal Mobile Telecommunications System (UMTS) (including, Long Term Evolution (LTE), LTE-A (Long Term Evolution-Advanced)), Global System for Mobile Communications (GSM), and the like.

By way of a non-limiting example only, further description will relate to a CDMA communication system, but such teachings apply equally to other system types including a CDMA wireless communication system as well as OFDM (Orthogonal Frequency Division Multiplexing) wireless communication system.

A CDMA wireless communication system generally includes one or more mobile terminals (MT or User Equipment, UE) 100, one or more base stations (BSs, NodeB, or evolved NodeB), one or more base station controllers (BSCs), and a mobile switching center (MSC). The MSC is configured to interface with a conventional Public Switched Telephone Network (PSTN) and the BSCs. The BSCs are coupled to the base stations via backhaul lines. The backhaul lines may be configured in accordance with any of several known interfaces including, for example, E1/T1, ATM, IP, PPP, Frame Relay, HDSL, ADSL, or xDSL. Hence, the plurality of BSCs can be included in the CDMA wireless communication system.

Each base station may include one or more sectors, each sector having an omni-directional antenna or an antenna pointed in a particular direction radially away from the base station. Alternatively, each sector may include two or more different antennas. Each base station may be configured to support a plurality of frequency assignments, with each frequency assignment having a particular spectrum (e.g., 1.25 MHz, 5 MHz, etc.).

The intersection of sector and frequency assignment may be referred to as a CDMA channel. The base stations may also be referred to as Base Station Transceiver Subsystems (BTSs). In some cases, the term "base station" may be used to refer collectively to a BSC, and one or more base stations. The base stations may also be denoted as "cell sites." Alternatively, individual sectors of a given base station may be referred to as cell sites.

A broadcasting transmitter (BT) transmits a broadcast signal to the mobile terminals 100 operating within the system. The broadcast receiving module 111 of FIG. 1 is typically configured inside the mobile terminal 100 to receive broadcast signals transmitted by the BT.

Global Positioning System (GPS) satellites for locating the position of the mobile terminal 100, for example, may cooperate with the CDMA wireless communication system. Useful position information may be obtained with greater or fewer satellites than two satellites. It is to be appreciated that other types of position detection technology, (i.e., location technology that may be used in addition to or instead of GPS location technology) may alternatively be implemented. If desired, at least one of the GPS satellites may alternatively or additionally be configured to provide satellite DMB transmissions.

Figure 3B:
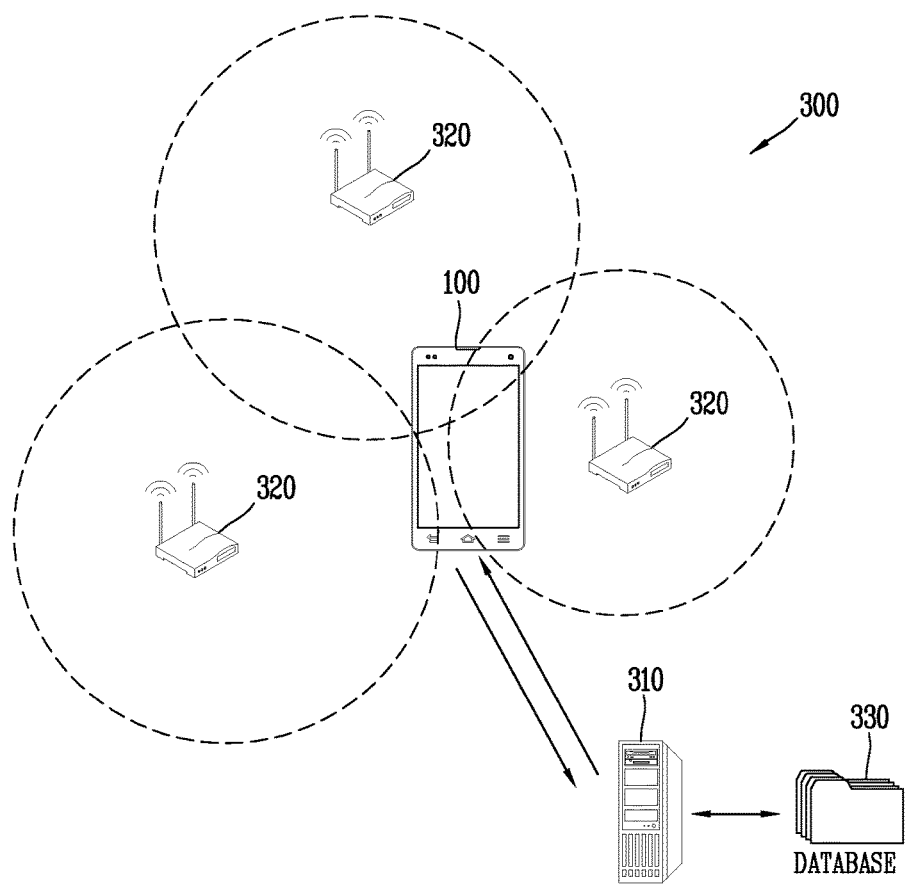

Next, a method to measure a position of the mobile terminal 100 according to the present invention will be explained with reference to FIG. 3B.

The location information module 115 is generally configured to detect, calculate, or otherwise identify a position of the mobile terminal. As an example, the location information module 115 may include a Global Position System (GPS) module, a Wi-Fi module, or both. If desired, the location information module 115 may alternatively or additionally function with any of the other modules of the wireless communication unit 110 to obtain data related to the position of the mobile terminal.

A typical GPS module 115 can measure an accurate time and distance from three or more satellites, and accurately calculate a current location of the mobile terminal according to trigonometry based on the measured time and distances. A method of acquiring distance and time information from three satellites and performing error correction with a single satellite may be used. In particular, the GPS module may acquire an accurate time together with three-dimensional speed information as well as the location of the latitude, longitude and altitude values from the location information received from the satellites. Furthermore, the GPS module can acquire speed information in real time to calculate a current position. Sometimes, accuracy of a measured position may be compromised when the mobile terminal is located in a blind spot of satellite signals, such as being located in an indoor space. In order to minimize the effect of such blind spots, an alternative or supplemental location technique, such as Wi-Fi Positioning System (WPS), may be utilized.

The Wi-Fi positioning system (WPS) refers to a location determination technology based on a wireless local area network (WLAN) using Wi-Fi as a technology for tracking the location of the mobile terminal 100. This technology typically includes the use of a Wi-Fi module in the mobile terminal 100 and a wireless access point for communicating with the Wi-Fi module.

The Wi-Fi positioning system may include a Wi-Fi location determination server, a mobile terminal, a wireless access point (AP) connected to the mobile terminal, and a database stored with wireless AP information.

The mobile terminal 100 connected to the wireless AP may transmit a location information request message to the Wi-Fi location determination server.

The Wi-Fi location determination server extracts the information of the wireless AP connected to the mobile terminal 100, based on the location information request message (or signal) of the mobile terminal 100. The information of the wireless AP may be transmitted to the Wi-Fi location determination server through the mobile terminal 100, or may be transmitted to the Wi-Fi location determination server from the wireless AP.

The information of the wireless AP extracted based on the location information request message of the mobile terminal 100 may include one or more of media access control (MAC) address, service set identification (SSID), received signal strength indicator (RSSI), reference signal received Power (RSRP), reference signal received quality (RSRQ), channel information, privacy, network type, signal strength, noise strength, and the like.

The Wi-Fi location determination server may receive the information of the wireless AP connected to the mobile terminal 100 as described above, and may extract wireless AP information corresponding to the wireless AP connected to the mobile terminal from the pre-established database. The information of any wireless APs stored in the database may be information such as MAC address, SSID, RSSI, channel information, privacy, network type, latitude and longitude coordinate, building at which the wireless AP is located, floor number, detailed indoor location information (GPS coordinate available), AP owner's address, phone number, and the like. In order to remove wireless APs provided using a mobile AP or an illegal MAC address during a location determining process, the Wi-Fi location determination server may extract only a predetermined number of wireless AP information in order of high RSSI.

Then, the Wi-Fi location determination server may extract (analyze) location information of the mobile terminal 100 using at least one wireless AP information extracted from the database.

A method for extracting (analyzing) location information of the mobile terminal 100 may include a Cell-ID method, a fingerprint method, a trigonometry method, a landmark method, and the like.

The Cell-ID method is used to determine a position of a wireless AP having the largest signal strength, among peripheral wireless AP information collected by a mobile terminal, as a position of the mobile terminal. The Cell-ID method is an implementation that is minimally complex, does not require additional costs, and location information can be rapidly acquired. However, in the Cell-ID method, the precision of positioning may fall below a desired threshold when the installation density of wireless APs is low.

The fingerprint method is used to collect signal strength information by selecting a reference position from a service area, and to track a position of a mobile terminal using the signal strength information transmitted from the mobile terminal based on the collected information. In order to use the fingerprint method, it is common for the characteristics of radio signals to be pre-stored in the form of a database.

The trigonometry method is used to calculate a position of a mobile terminal based on a distance between coordinates of at least three wireless APs and the mobile terminal. In order to measure the distance between the mobile terminal and the wireless APs, signal strength may be converted into distance information, Time of Arrival (ToA), Time Difference of Arrival (TDoA), Angle of Arrival (AoA), or the like may be taken for transmitted wireless signals.

The landmark method is used to measure a position of a mobile terminal using a known landmark transmitter. In addition to these position location methods, various algorithms may be used to extract (analyze) location information of a mobile terminal. Such extracted location information may be transmitted to the mobile terminal 100 through the Wi-Fi location determination server, thereby acquiring location information of the mobile terminal 100.

The mobile terminal 100 can acquire location information by being connected to at least one wireless AP. The number of wireless APs required to acquire location information of the mobile terminal 100 may be variously changed according to a wireless communication environment within which the mobile terminal 100 is positioned.

A detection unit 181 of the mobile terminal 100 according to an embodiment of the present invention which includes at least one of the aforementioned components, is configured to monitor a stress index calculated based on a user's biometric information, and to detect a time point when the increased stress index has been decreased as a result of the monitoring, thereby detecting a first section where a decrease rate of the stress index exceeds a reference range. That is, the detection unit 181 detects a section where increased stress is efficiently decreased by an external situation (e.g., exercise, sleep, shopping, etc.)

Then, the memory 170 stores therein context information corresponding to the first section. The context information means at least one of a position of the mobile terminal 100, a user's state information, a user's motion information, and surrounding environment information, at the first section. Such context information may be accumulatively stored whenever the first section is detected, thereby configuring database (DB).

At a section where the increased stress index has been decreased, if a second section where a decrease rate of the increased stress index is less than a reference range occurs, the controller 180 of the mobile terminal 100 outputs stress relief information generated based on the context information stored in the memory 170. That is, when a decrease of the stress is delayed, the controller 180 outputs stress relief information using stored context information. The stress relief information may be at least one of a message which guides a stress index decreasing situation corresponding to the context information stored in the memory 170, an image, and a graphic change.

The mobile terminal 100 according to the present invention does not collect context information at all sections where stress is decreased, but collects context information only at a section where stress is efficiently decreased by an external situation. And the mobile terminal 100 does not provide a stress relief service at all sections where stress is increased, but provides a stress relief service using collected context information only when a decrease of stress is delayed.

With such a configuration, only context information, which has occurred from a section where a stress index has been efficiently decreased based on a user's biometric information, is collected, and the collected context information is provided at a time point when a decrease of the stress index is delayed. This may allow stress to be reduced more efficiently, and may provide a service specialized for a user.

Hereinafter, with reference to FIGS. 4, 5A and 5B, will be explained a method for providing a stress relief service based on a user's biometric information, by the mobile terminal 100 according to an embodiment of the present invention.

Figure 4:
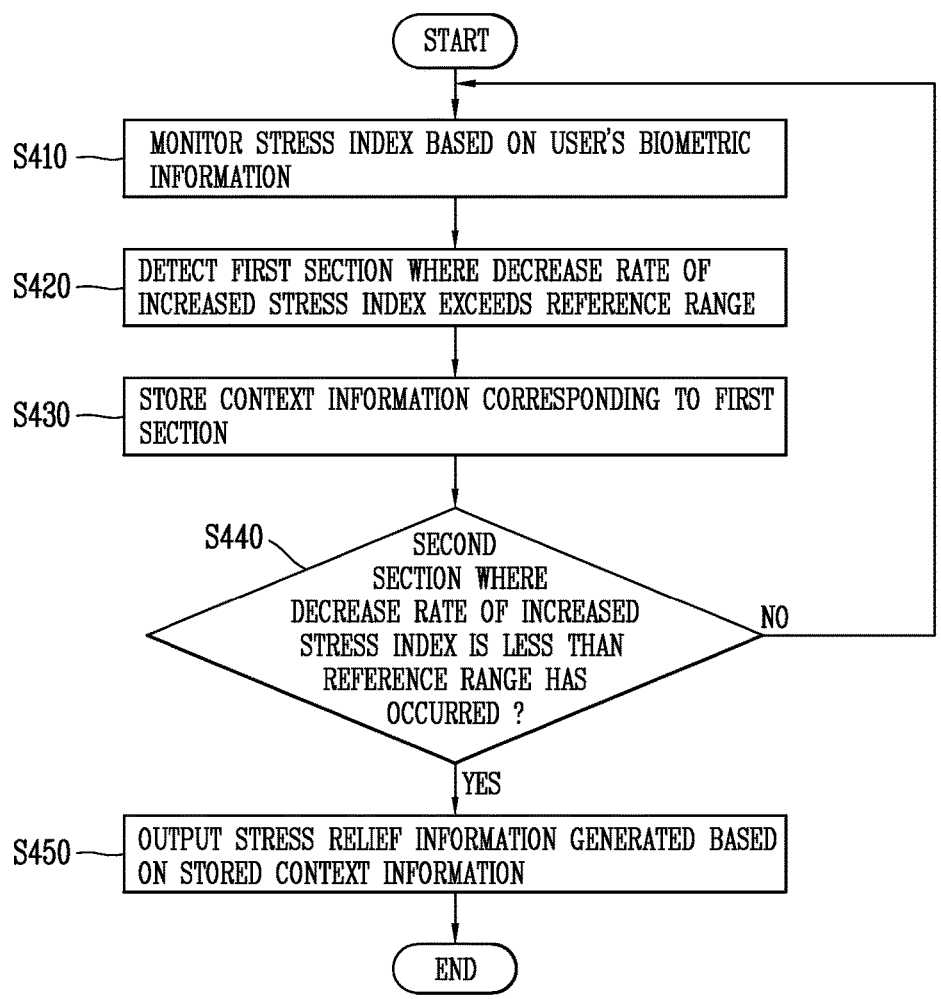
FIG. 4 is a representative flowchart for explaining a method for providing a stress relief service based on a user's biometric information, in a mobile terminal according to the present invention.

Referring to FIG. 4, the mobile terminal 100 may monitor a stress index based on a user's biometric information (S410).

For this, the mobile terminal 100 may sense a user's biometric information by the sensing unit 140, or may receive a user's biometric information sensed by an external sensor, through the wireless communication unit 110.

In the case where a user's biometric information is sensed by the mobile terminal 100, the mobile terminal 100 may be implemented as a wearable device mounted to a specific part of a user's body and configured to sense a user's biometric signal through various sensors.

The biometric information may mean an electric signal generated from a body of a user who has worn the mobile terminal 100 or an external device (e.g., a link) which wirelessly communicates with the mobile terminal 100. The electric signal may be one of an electrocardiogram (ECG) signal, a photoplethymogram (PPG) signal, and a galvanic skin response (GSR) signal, but is not limited to this. That is, the electric signal may include various types of signals widely used by those skilled in the art in order to measure a stress index. For instance, as a body temperature sensor, a cardiac impulse (heart rate) sensor, a pressure sensor, etc. are further provided at the mobile terminal 100, biometric information may be further obtained by the sensors.

More specifically, an electrocardiogram (ECG) signal is an electric signal occurring from the surface of the skin, which indicates an electric activity of the heart. The ECG signal may be measured by inducing an activity current occurring from the heart muscle to two proper positions on the surface of the body according to a heart rate. A psychological state of a user who has worn the mobile terminal 100 may be recognized by observing a period of the ECG signal and a characteristic of a waveform change.

An electromyogram (EMG) signal is an electric signal occurring from the surface of the skin, which indicates a contractile force of the muscle, a muscular activity, and a fatigue degree. The EMG signal may be sensed based on a movement of tendons due to a movement of fingers of a user who has worn the mobile terminal 100. More specifically, finger flexor tendons of tendons which control a movement of each finger exists in a user's wrist (or at a carpal tunnel). The finger flexor tendons have nine tendons and one nerve.

If a finger moves, the nine tendons included in the finger flexor tendons move in a variously-combined manner. For instance, sensors of the mobile terminal 100 may sense a shape of tendons transformed according to a movement of a finger or a wrist. In this case, the controller may determine a gesture by fingers based on the sensed information.

An electroencephalogram (EEG) signal is an electric signal occurring from the surface of the skin, which indicates concentration or a brain activity with respect to an external stimulus. The EEG signal may be measured by inducing a potential change occurring from the cerebrum, or a brain current occurring due to the potential change, onto the scalp.

The EEG signal may be categorized into six types according to a frequency characteristic. Generally, a delta type indicates a 'sleeping state', a theta type indicates a 'drowsy state', an alpha type indicates a 'comfortable state', a low beta type indicates a 'concentrated state', an intermediate beta type indicates an 'alert state', and a high beta type indicates an 'excited state'. That is, a user's psychological state may be determined based on the EEG signal.

A galvanic skin reflex (GSR) signal is an electric signal occurring from the surface of the skin, which indicates a change of a skin resistance to activation of sympathetic nerves. The GSR signal may be obtained by measuring that an electric resistance generated by an external stimulus or an emotional excitement is temporarily reduced on the skin of the body, or by measuring occurrence of an activation potential on the skin of the body. Once a sympathetic nervous system is activated as a user becomes tense or alert, sweat glands on the surface of the skin are activated. This may increase conductivity and GSR.

A heart rate variability (HRV) is an electric signal occurring from the surface of the skin, which indicates a change of an interval (RRI: R-R interval) between an R peak and an R peak of an ECG. A frequency domain power spectrum of the HRV may be obtained by converting time-series signals of the RRI through a Fourier transform method. A low frequency domain (0-0.15 Hz) of the power spectrum mainly reflects an activity of a sympathetic nervous system, and a high frequency domain (0.15-0.4 Hz) indicates an activity of a parasympathetic nervous system.

A photoplethysmogram (PPG) signal is an electric signal obtained by measuring that an arterial blood volume in blood vessels at a finger tip is increased and decreased repeatedly according to a heart rate. Transmission light detected by a light receiving portion provided at a finger tip is received, in a state where a light amount absorbed by the finger is deducted from the transmission light, and is represented as a waveform of a blood flow change according to a heart rate. Such a waveform is the PPG.

A physical state and a psychological state of a user who has worn the mobile terminal 100 may be determined based on a correlation among the sensed various biometric information. The biometric information may be stored together with context information and time information. If such information is accumulated for a predetermined time period, meaningful group data related to a user's life style may be obtained.

The mobile terminal 100 may calculate a user's stress index by analyzing such biometric information. For instance, the mobile terminal 100 may determine whether a current stress index is lower or higher than usual, and an increased or decreased degree of the current stress index, by analyzing a frequency domain and/or a time domain of HRV. If such analyses are accumulated for a predetermined time period, the mobile terminal 100 may calculate a user's average stress index. As a result, the mobile terminal 100 may recognize a user's stress pattern, e.g., a specific time when a user is under high stress, or an average time taken for the user to recover from the stress (to relieve the stress).

Then, the detection unit 181 of the mobile terminal 100 detects a first section where a decrease rate of the increased stress index exceeds a reference range, based on a result of the monitoring (S420). That is, the detection unit 181 detects a section where stress is relieved more rapidly than usual (i.e., 'efficient recovery section').

Here, the reference range means a stress index decrease rate corresponding to a time taken for a user to naturally relieve increased stress without depending on an external situation. Such a stress index decrease rate may be variable according to a user's sex, age, job, etc. Therefore, in the present invention, the reference range may be determined based on a personal stress pattern generated based on biometric information accumulated for a predetermined time period.

For instance, it takes 5 minutes for user A to relieve stress, whereas it takes more than 10 minutes for user B to relieve stress. In this case, a stress index decrease rate of the user A is relatively higher. Accordingly, the mobile terminal 100 may set a high reference range to the user A, and may set a reference range lower than that of the user A to the user B.

Once the first section is detected, the controller 180 collects context information corresponding to the first section, and provides the collected context information to the memory 170 (S430). Such a task is repeatedly performed whenever the first section is detected.

The context information means information related to at least one of a position of the mobile terminal (e.g., home or company), an operation state of the mobile terminal 100 (e.g., music play, album display, etc.), a user's state (e.g., sleeping, activity, psychological state, etc.), a user's movement (e.g., exercise, walking, etc.) and surrounding environment (e.g., weather, external noise, noise degree, etc.), at the first section, i.e., at the efficient recovery section. Alternatively, the context information may include user's various preference information on music, place, food, etc., preference information of many users who have a similar life pattern to the user, etc.

The context information may be collected according to a user's situation, by place, and by time. And the context information may be collected by driving various sensors of the mobile terminal 100, or through a user's input.

The controller 180 ignores context information collected at a section where a decrease rate of an increased stress index is less than a reference range. That is, the controller 180 collects only context information corresponding to an efficient recovery section, i.e., a section where an increased stress index has been efficiently decreased by an external situation.

Figure 5A:
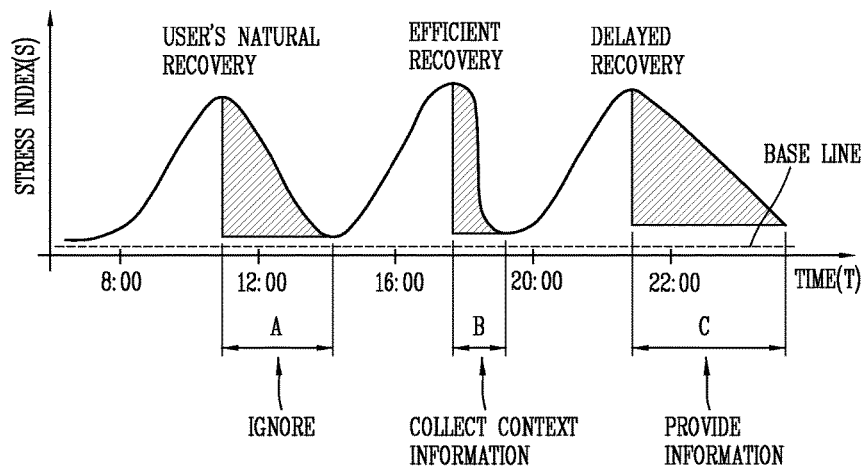
FIGS. 5A and 5B are views for explaining a method for extracting context information from a section where a stress index is efficiently decreased, in a mobile terminal according to the present invention.

FIG. 5A illustrates a method for extracting context information from a section where a stress index is efficiently decreased. That is, FIG. 5A illustrates various examples to relive an increased stress index.

FIG. 5A illustrates a stress curve indicating an increase and a decrease of stress based on a user's biometric information sensed for a day.

Referring to FIG. 5A, a starting point of each of sections 'A', 'B' and 'C' is a time point when a stress index increased to more than a reference value starts to be decreased. And an ending point of each of the sections 'A', 'B' and 'C' is a time point when the decreased stress index reaches a preset minimum value, i.e., a base line. In the present invention, context information is not collected at all sections where an increased stress index is deceased, but is collected only at the section 'B'.

For this, the mobile terminal 100 may operate sensors required to collect context information, at a time point when the section 'B' is detected. For instance, if the section 'B' is detected while a stress index is being monitored, the mobile terminal 100 may collect various context information by driving the location information module, the cameras, etc. thereof, and may trigger a control command for storing the collected context information.

More specifically, the section 'A' shows a case where an increased stress index is naturally decreased, which illustrates a stress decrease rate corresponding to the aforementioned reference range. The section 'A' may be referred to as a 'natural recovery section'. In the section where stress is relieved naturally by an antagonism of the human body, it is not required to collect context information.

The section 'B' shows a case where an increased stress index is efficiently decreased by an external situation, which illustrates a stress decrease rate exceeding the aforementioned reference range. The section 'B' corresponds to an 'efficient recovery section'. In the section 'B', a gradient is steeper than that in the section 'A'. That is, an increased stress index is rapidly relieved by an external situation. If context information collected in the section 'B' is provided to a user, stress may be relieved rapidly and efficiently.

Whether a stress index has been rapidly relieved or not may be determined at a time point when the stress index has reached a base line. Therefore, a time point when the section 'B' is substantially detected may be a time point when the section 'B' is terminated or a time point after that. Thus, the mobile terminal 100 may reversely calculate a time point when the stress index has reached a peak, based on a time point when the stress index has reached the base line, thereby obtaining time taken for the stress index to be efficiently relieved. And various sensors may be driven to collect context information, at a time point when the section 'B' has been substantially detected.

The section 'C' shows a case where a decrease of an increased stress index is delayed, which illustrates a stress decrease rate less than the aforementioned reference range. The section 'C' may be referred to as a 'delayed recovery section'. In the section 'C', stress relief information based on the context information in the section 'B' is provided to reduce stress, as will be explained later.

Figure 5B:
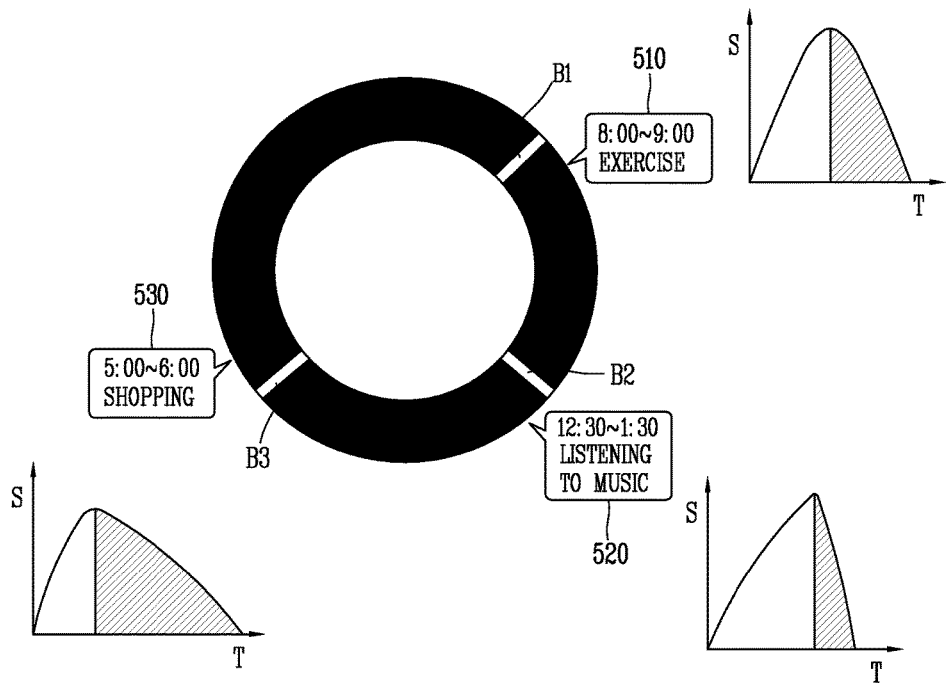

FIG. 5B illustrates an example of various context information collectable when the section 'B' is detected. Referring to FIG. 5B, sections 'B1', 'B2' and 'B3' show different efficient recovery sections. That is, three efficient recovery sections have been detected, and context information indicating 'exercise', 'listening to music' and 'shopping' has been collected. Such context information may be collected together with time information.

When an efficient recovery section has a steeper gradient, the efficient recovery section may be more efficient. Therefore, it can be seen that the section 'B2' is the most efficient recovery section. That is, in FIG. 5B, a user's stress index may be relieved (removed) the most efficiently when the user listens to music.

In FIG. 5B, stress may be relieved efficiently in the morning through 'exercise', and stress may be relieved efficiently in the afternoon through 'listening to music'.

Once context information corresponding to sections where stress has been efficiently reduced is stored, the controller 180 may detect occurrence of a second section where a decrease rate of an increased stress index is less than a reference range (S440). That is, the controller 180 may detect a section where relief (removal) of the stress index is delayed.

More specifically, the controller 180 may detect the second section at a time point when it is sensed that the stress index has not reached the base line (refer to FIG. 5A) in a state that a decrease rate of the stress index is less than a reference range. That is, in FIG. 5A, a time point when the section 'C' is substantially detected may be an intermediate region of the section 'C'.

Once the occurrence of the second section is detected, the controller 180 may generate stress relief information based on the stored context information, and outputs the generated stress relief information through the output unit (S450). For this, the controller 180 may generate a trigger signal for extracting the stored context information.

In an embodiment, as a result of monitoring a stress index, the controller 180 may output notification information at a time point when the increased stress index has exceeded a reference range. Accordingly, a user may recognize that his or her stress index has increased. If a reference time (a time corresponding to the natural recovery section) lapses after the notification information is output, the controller 180 may output stress relief information generated based on the stored context information, through the display unit 151 of the mobile terminal 100.

The stress relief information may be at least one of a message which guides a stress index decreasing situation corresponding to the stored context information, an image, and a graphic change. And the stress relief information is provided in a manner to recommend a user with a situation the same as or similar to the stored context information.

For instance, the stress relief information may be displayed on a pop-up window including selection icons to select for information reception and non-reception.

If an input to the selection icon on the pop-up window is received, the controller 180 provides a service related to the stress relief information, and measures a time taken for the increased stress index to be relieved. Once the stress is relieved, the controller 180 stores the measured time in the memory 170, together with the stored context information.

Figure 6:
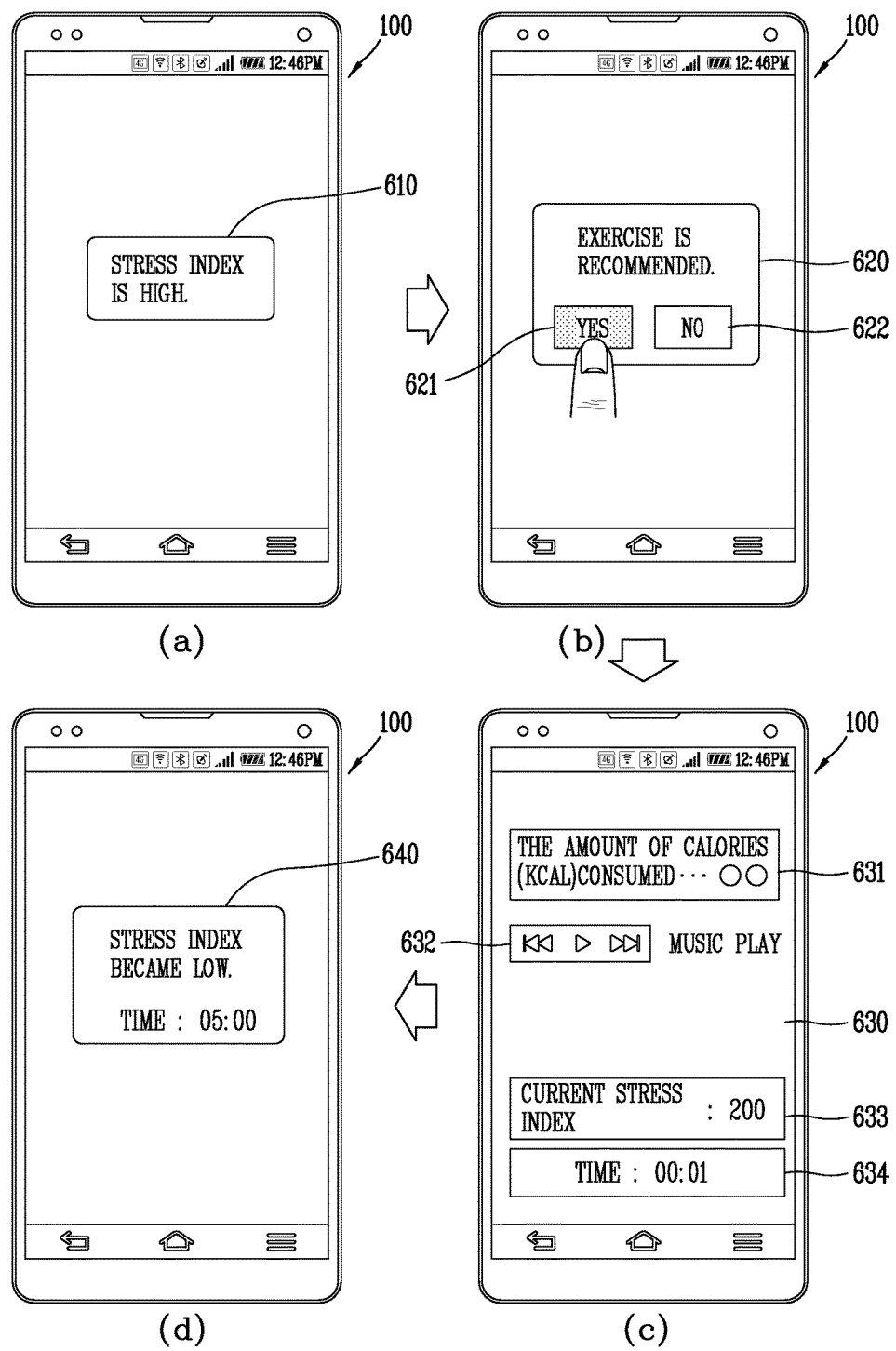
FIG. 6 is a conceptual view for explaining the flowchart of FIG. 4.

FIG. 6 is a conceptual view for explaining the flowchart of FIG. 4.

As shown in FIG. 6A, if it is detected that a stress index has been increased to more than a reference value, as a monitoring result based on a user's biometric information, notification information 610 indicating the increase of the stress index is popped-up on the display unit 151.

Then, the controller 180 measures a time taken for the stress index to be relieved, from the time point when the notification information 610 has been popped-up. That is, even if the stress index is increased, the controller 180 waits for a time taken for the stress index to be naturally relieved (i.e., a time corresponding to a termination point of the natural recovery section).

If it is detected that the stress index has not been relieved even after lapse of the time, the controller 180 outputs a pop-up window 620 inducing context information corresponding to an efficient recovery section (e.g., 'exercise'), on the display unit 151, as shown in FIG. 6B.

Here, the pop-up window 620 is displayed in a manner to recommend stress relief information. That is, if 'No' 622 is selected from the pop-up window 620 shown in FIG. 6B, information may not be provided any longer such that a user may relieve stress for himself or herself.

On the contrary, if 'Yes' 621 is selected from the pop-up window 620, the mobile terminal 100 may convert an operation state of the mobile terminal such that a user may perform an operation the same as the stored context information. For instance, as shown in FIG. 6C, on the display unit 151, may be displayed screen information 630 including an indicator bar 631 indicating the amount of calories consumed (kcal), a play bar 632 for playing music frequently played when the user does exercise, a notification icon 633 indicating a current stress index, and a time icon 634 indicating a time lapsed from a time point when stress relief information has been provided.

If it is detected that the stress index has been relieved, the mobile terminal 100 may output a pop-up window 640 indicating the relief of the stress index, as shown in FIG. 6D. The pop-up window 640 may display time information about a time taken from the time point when the stress relief information has been provided, to a time point when the stress index has been relieved. The controller 180 may record the displayed time information on the extracted context information.

The context information stored in the memory 170 may be updated and learned. For this, if a section where a decrease rate of the increased stress index is larger than that in the first section is detected by the detection unit 181, the controller 180 may update the context information stored in the memory. In this case, the controller 180 may replace the pre-stored context information by newly-stored context information in an overwriting manner, or may provide a priority such that newly-stored context information may be firstly extracted.

After outputting the stress relief information, the controller 180 may store or update additional information such as the number of times that a plurality of context information stored in the memory 170 has been extracted, and a time taken for the stress index has been relieved.

In a case where a plurality of context information has been stored in the memory 170, the controller 180 may extract specific context information preferentially or selectively, based on a preset reference.

For this, the plurality of context information corresponding to the 'efficient recovery section' (first section) may be categorized by time or place. In this case, if the 'delayed recovery section' (second section) occurs, the controller 180 may generate stress relief information, by preferentially extracting context information stored at a time corresponding to an occurrence time point of the second section (substantially, a detection time point of the second section), or context information stored at a position corresponding to an occurrence time point of the second section (substantially, a detection time point of the second section).

As another example, if the 'delayed recovery section' (second section) occurs, the controller 180 may generate stress relief information, by preferably extracting context information having a large decrease rate of the stress index, among the stored context information.

Although not shown, while the mobile terminal 100 is monitoring a stress index based on a user's biometric information (the mobile terminal can be set to monitor a stress index only in a recording mode), if a section where the stress index increased to more than a reference value has been rapidly relieved (i.e., an efficient recovery section) is detected, the controller 180 may output, to the display unit 151, an input region for directly inputting context information such as a user's situation and surrounding environment information.

If the efficient recovery section is detected, the controller 180 may output, to the display unit 151, a message for confirming whether context information collected through various sensors is consistent with a substantial situation or not (e.g., 'Have you gone jogging?'). This may allow context information to be collected more precisely.

So far, has been explained a method for selectively collecting context information based on a time taken for an increased stress index to reach a base line (reference value). As aforementioned, the base line (reference value) is variable according to a user. That is, a high base line (reference value) may be set to a user who usually has a high stress index. On the other hand, a low base line (reference value) may be set to a user who usually has a low stress index.

Hereinafter, will be explained a method for providing a stress relief service or an emergency service by extracting context information at a section where a stress index is less than a base line (reference value).

Figure 7:
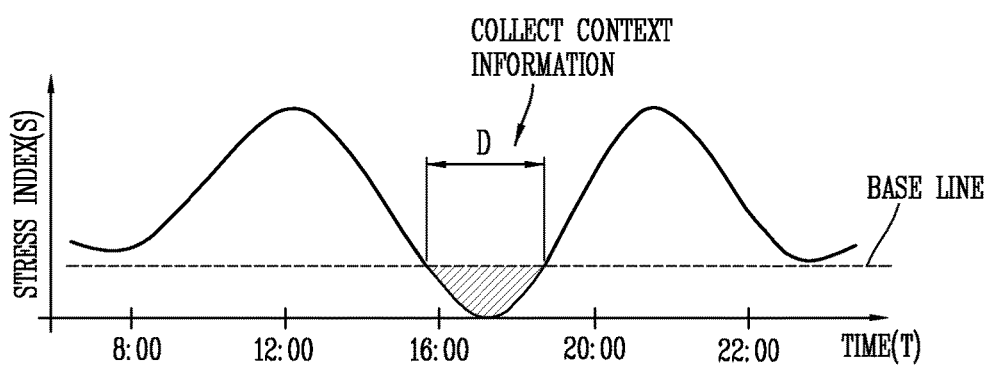
FIG. 7 is a graph for explaining a method for extracting context information from a section where a stress index is less than a reference value.

Referring to a stress curve shown in FIG. 7, section 'D' may be defined as a section where a stress index is less than a base line. That is, the section 'D' means a case where a user's stress index is lower than a minimum stress index. Here, context information, corresponding to the case where a user's stress index is lower than a minimum stress index, may be collected to provide stress relief information.

For this, the detection unit 181 of the mobile terminal 100 may detect a third section (hereinafter, will be referred to as 'bottom section') where a stress index is less than a predetermined minimum value (i.e., a base line). As shown in FIG. 7, in the bottom section, a stress index may be increased or decreased. That is, the bottom section may be defined as a time duration for which a stress index calculated based on biometric information is less than a base line. The case where the stress index is absolutely low is unusual, which may result from an external situation or when a user's body is abnormal. However, if the bottom section is low than a reference value for a short time duration, such a case may be regarded as a temporal phenomenon, and the collected context information may be ignored.

Once the bottom section is detected, the memory 170 may further store therein second context information corresponding to the detected bottom section (third section). In this case, the second context information is stored in a distinguished manner from the context information corresponding to the efficient recovery section.

The second context information may be related to a user's specific situation, a time and a place while the stress index is within a range of the 'bottom section'. For instance, the second context information may be limited information specific to a user, such as a user's smelling specific fragrance or a user's listening to specific music.

Next, if the stress index does not reach the minimum value (i.e., the base line) within a preset time after outputting the context information corresponding to the efficient recovery section, the controller 180 may generate second stress relief information based on the stored second context information, and may output the second stress relief information. In this case, contrary to the first stress relief information implemented in a 'recommendation' manner, the second stress relief information may be implemented in a manner to 'provide' a stress relief service more directly and positively, by changing an operation state of the mobile terminal.

Figure 11:
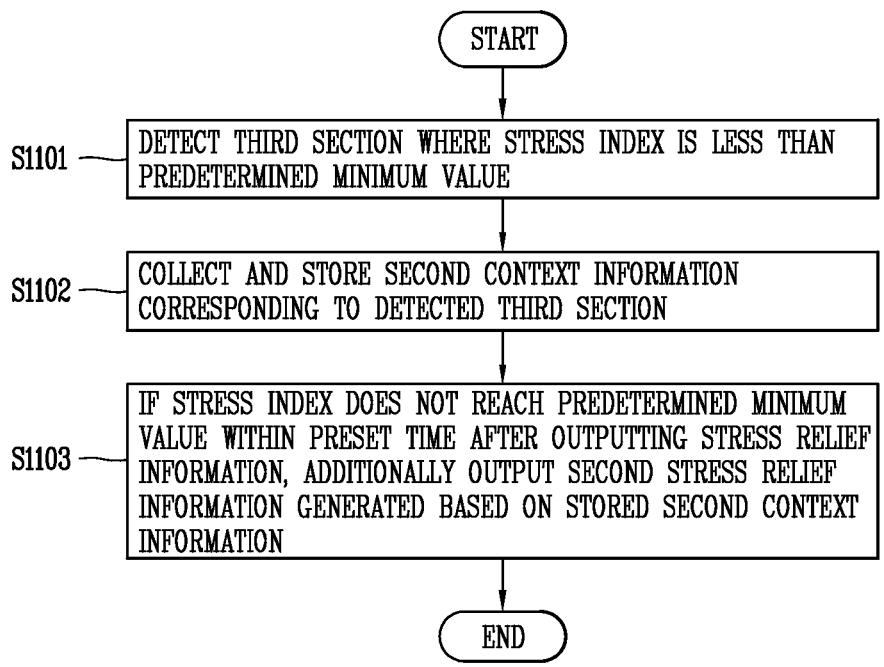
FIG. 11 is a flowchart for explaining a method for providing a stress relief service related to context information corresponding to a section where a stress index is decreased to a level less than a reference value, in relation to FIG. 7.

FIG. 11 is a flowchart for explaining a method for providing a stress relief service related to context information corresponding to a section where a stress index is decreased to less than a reference value, in relation to FIG. 7.

Referring to FIG. 11, as a result of monitoring a stress index based on a user's biometric information, the mobile terminal 100 may detect a third section where the stress index increased and then decreased is less than a preset minimum value (base line) (S1101).

Then, the controller 180 collects second context information corresponding to the detected third section, and stores the collected second context information in the memory 170 (S1102). In this case, the second context information is stored in a distinguished manner from the context information corresponding to the first section. The controller 180 ignores context information collected at a section where a decrease rate of the increased stress index is less than a reference range.

If a delayed recovery section occurs, the controller 180 may output stress relief information generated based on the context information corresponding to the first section. If the stress index does not reach the minimum value (base line) within a preset time, after outputting the stress relief information, the controller 180 may further output second stress relief information generated based on the stored second context information (S1103).

A user's health index may be calculated based on a differently-set base line (reference value). If a bottom section is maintained for a long time, it may be determined that a user's health has a problem. In this case, a message is provided to the user (e.g., a message is output to inquire whether it is an emergency). Then an automatic message is transmitted to an emergency medical treatment center or a medical institution based on collected context information, based on a response of the user or after a predetermined time lapses. Alternatively, a call may be connected to a registered acquaintance.

Figure 8A:
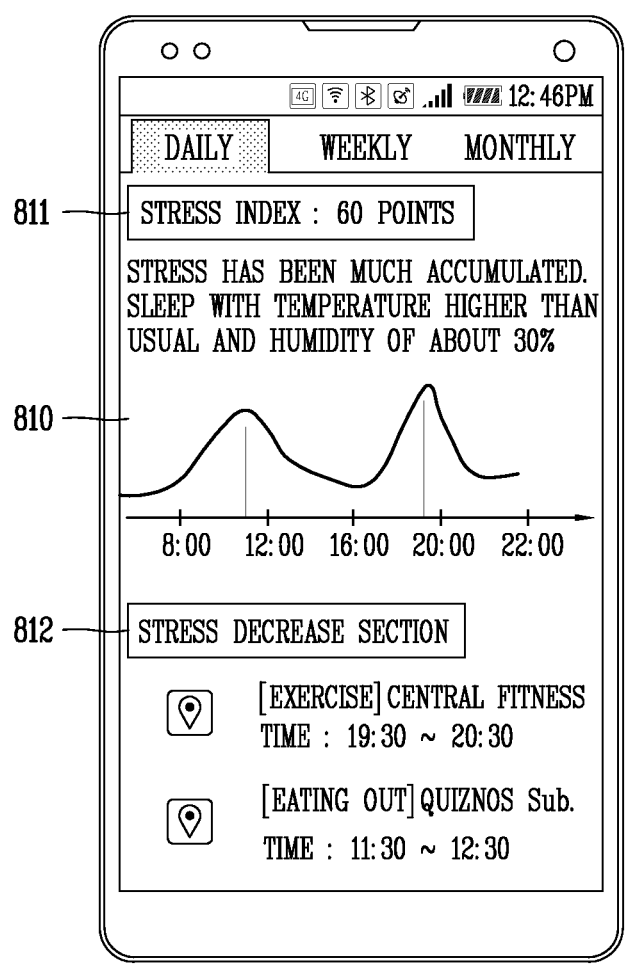
FIGS. 8A, 8B and 8C are conceptual views for explaining a method for displaying a stress relief pattern, in a mobile terminal according to the present invention.
Figure 8B:
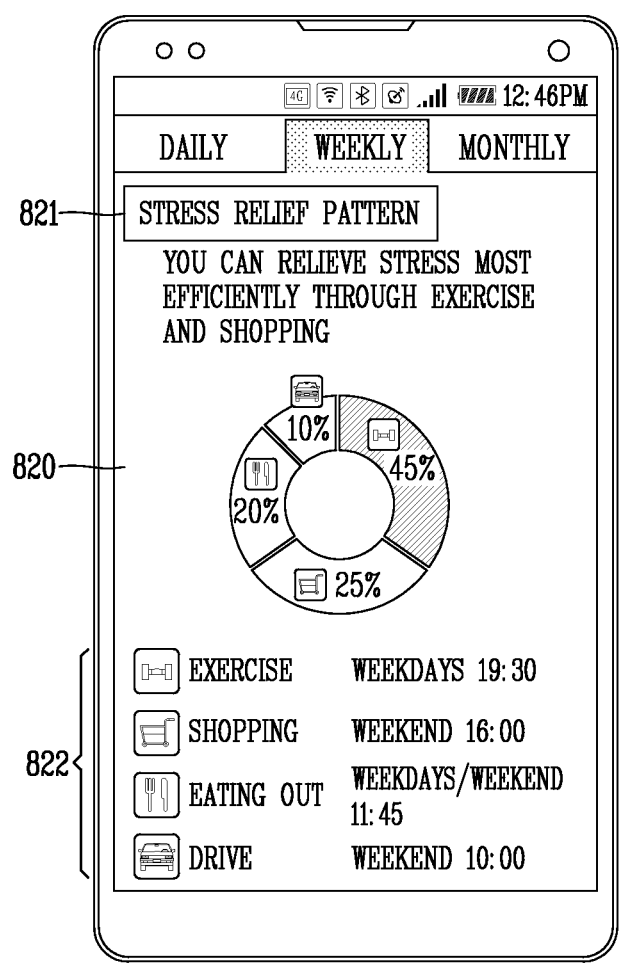
Figure 8C:
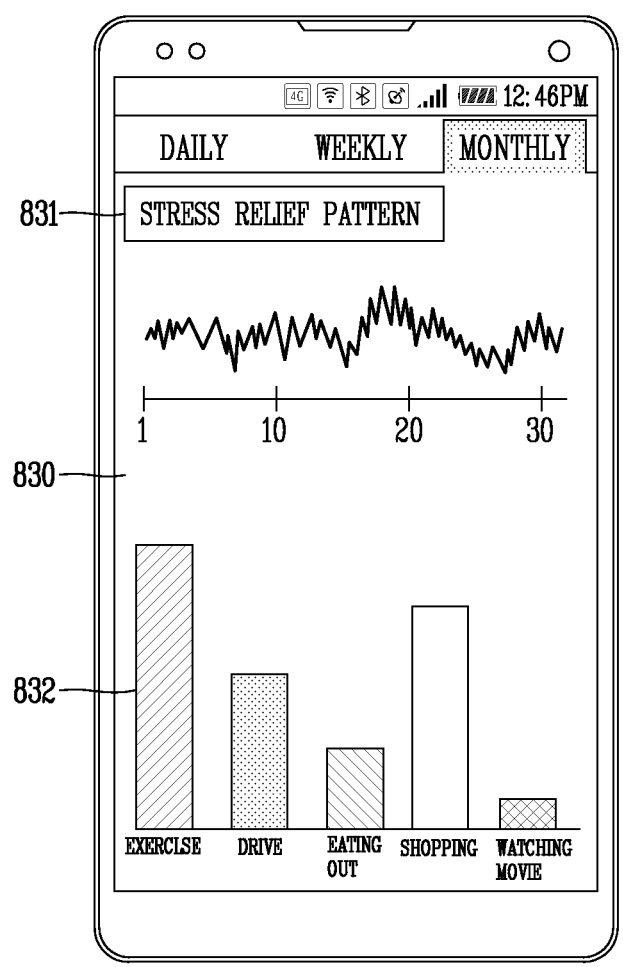

FIGS. 8A to 8C are conceptual views for explaining a method for displaying a stress relief pattern generated based on an efficient recovery section, in the mobile terminal according to the present invention.

The controller 180 of the mobile terminal 100 may obtain a user's personalized stress pattern, based on biometric information sensed (received) for a preset time.

The controller 180 may generate a stress relief pattern, based on context information corresponding to an efficient recovery section (or an efficient recovery section including a bottom section).

The stress relief pattern is obtained by grouping the same or similar context information detected for a reference time and corresponding to an efficient recovery section (or an efficient recovery section including a bottom section). The stress relief pattern may include a time taken for a stress index to be relieved in a specific situation, the number of times that the same or similar situation has repeatedly performed in the efficient recovery section, time information and position information corresponding to a specific situation, a recommended order of stress relief information, etc.

For this, the memory 170 may further store therein time information corresponding to the efficient recovery section, at the time of storing context information.

Once a predetermined input is received, the controller 180 may output the stress relief pattern to the display unit 151, based on the stored time information.

For instance, referring to FIG. 8A, when the mobile terminal enters a 'stress relief pattern' viewing mode, a stress curve is displayed based on a user's biometric information sensed for a day. In this case, on the display unit 151, may be popped-up screen information 810 including average stress index information 811, and information 812 indicating an efficient recovery section and corresponding situation information.

Here, if an input to select a reference time is received on the screen information 810 output to the display unit 151, e.g., if a touch is applied to a display region of 'DAILY', 'WEEKLY', or 'MONTHLY', the controller 180 reconfigures the stress relief pattern, based on a plurality of context information accumulated for a reference time corresponding to the input. Then, the controller 180 outputs a graphic object indicating the reconfigured stress relief pattern, to the display unit 151.

The graphic object may be a graph showing accumulated information of the same or similar context information for a selected reference time, on the generated stress relief pattern.

For instance, as shown in FIG. 8B, if 'WEEKLY' is selected as a reference time, accumulated information of context information detected for a week and corresponding to an efficient recovery section is displayed on the display unit 151. More specifically, on the display unit 151, may be displayed screen information 820 including information 821 which synthetically explains a stress relief pattern for a week, graph information indicating a ratio of accumulated same or similar context information, and recommendation information 822 to stress relief information when relief of a stress index is delayed.

If an input is applied to a specific item included in the recommendation information 822, the controller 180 may convert an operation state of the mobile terminal so as to induce a situation corresponding to the specific item. For instance, 'eating out' is selected, may be displayed screen information indicating places to dine, menus, locations, etc. for a week.

Referring to FIG. 8C, if 'MONTHLY' is selected as a reference time, on the display unit 151, may be displayed screen information 830 including graph information 831 indicating a stress relief pattern for a month, and graph information 832 indicating an accumulated degree of corresponding same or similar context information.

The mobile terminal 100 may store location information of the mobile terminal obtained through the location information module together with context information, thereby displaying the corresponding location information together when displaying the stress relief pattern.

Further, when a delayed recovery section occurs, the controller 180 may generate stress relief information by correlating a current position of the mobile terminal obtained through the location information module with stored context information. For instance, when 'exercise' is provided as stress relief information at the delayed recovery section, a gymnasium, a health club, or the like close to a current position of the mobile terminal may be displayed.

Figure 9:
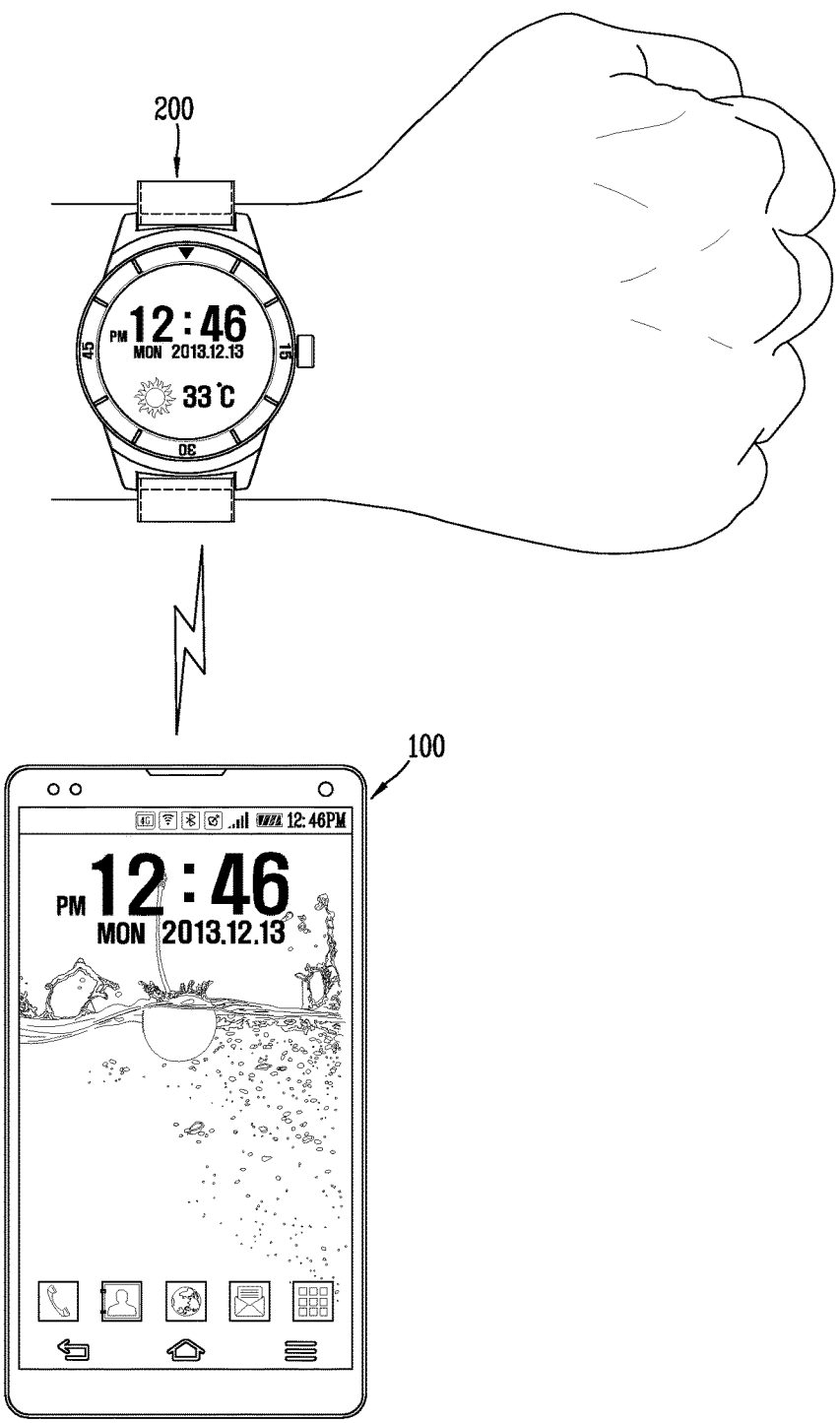
FIGS. 9, 10A, 10B and 10C are conceptual views for explaining a method for providing a stress relief service by using an external device connected to a mobile terminal according to the present invention.
Figure 10A:
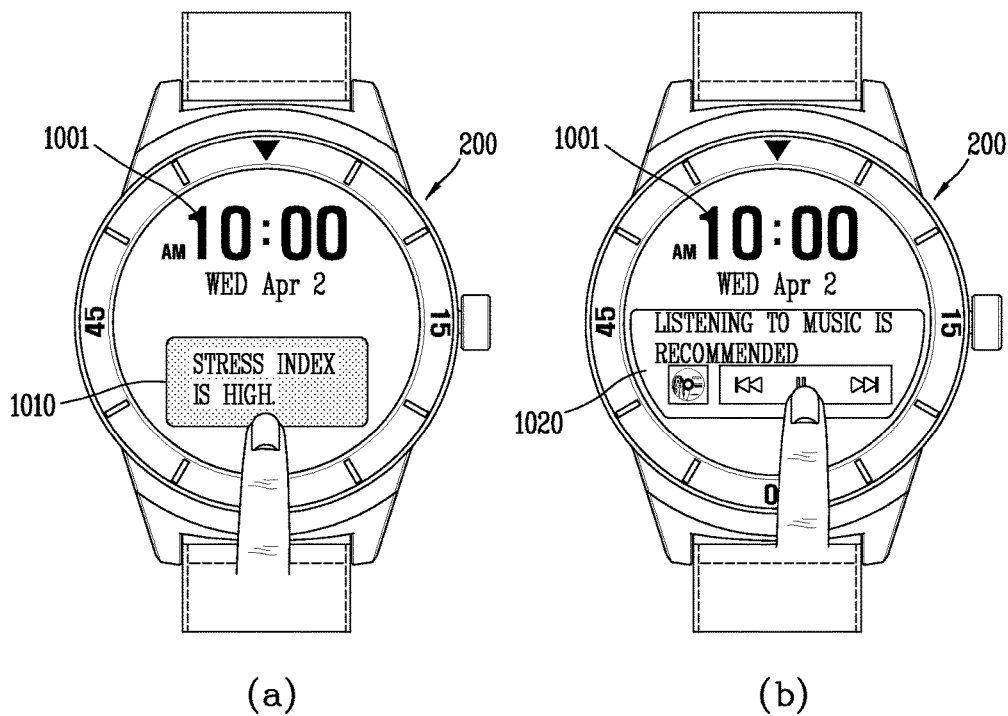
Figure 10B:
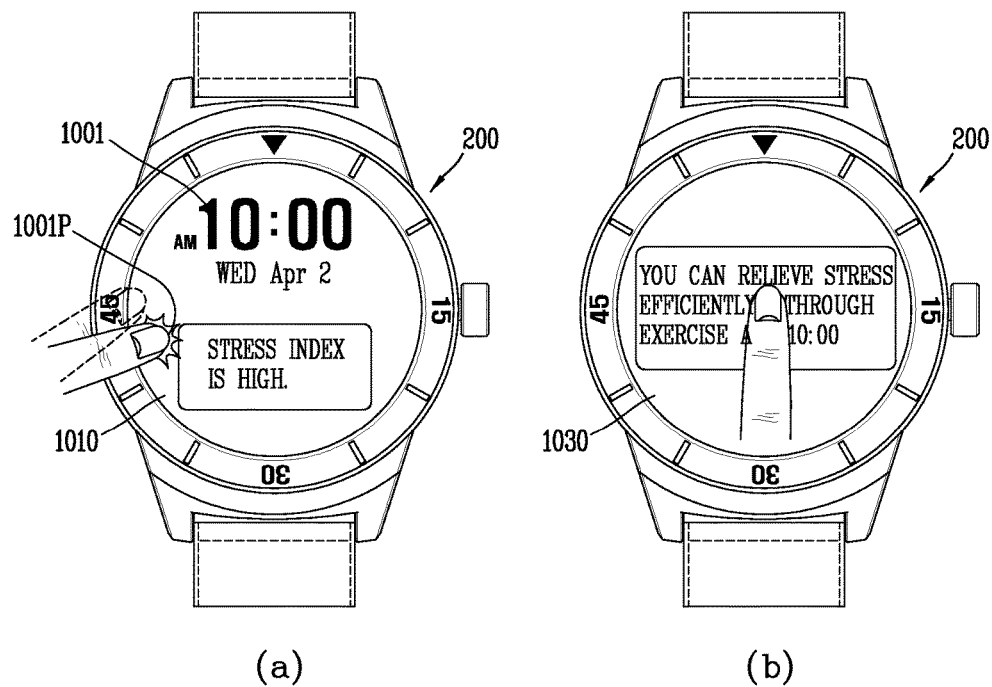

FIGS. 9, 10A and 10B are conceptual views for explaining a method for providing a stress relief service by using an external device connected to the mobile terminal according to the present invention. Here, the external device is implemented as a watch-type mobile terminal 200. However, the present invention is not limited to this. That is, the external device may be implemented as another type of mobile terminal.

Referring to FIG. 9, the mobile terminal 100 and the watch-type mobile terminal 200 may be connected to each other, through wireless communication units provided thereat. In this case, the mobile terminal 100 may receive a user's biometric information sensed through sensors of the watch-type mobile terminal 200. Then, the detection unit 181 of the mobile terminal 100 may monitor a stress index based on the received biometric information. In another embodiment, it is possible for the watch-type mobile terminal 200 to monitor biometric information sensed by the watch-type mobile terminal 200, and to transmit the biometric information to the mobile terminal 100 when a stress index has been increased to more than a reference value as a monitoring result.

If a delayed recovery section occurs as a result of monitoring the stress index in a connected state between the mobile terminal 100 and the watch-type mobile terminal 200, the controller 180 transmits a notification signal indicating a delayed state of a decrease of the stress index, to the watch-type mobile terminal 200, through the wireless communication unit 110.

As a result, as shown in FIG. 10A, a notification message 1010 such as 'Stress index is high' is popped-up on a display unit of the watch-type mobile terminal 200.

In response to an input applied from the watch-type mobile terminal 200 which has received the notification signal, the controller 180 of the mobile terminal 100 may generate stress relief information based on context information stored in an efficient recovery section, and may control the wireless communication unit 110 such that the generated stress relief information may be output from the watch-type mobile terminal 200.

In this case, the stress relief information to be output from the watch-type mobile terminal 200 may be changed according to a touch point on a touch screen of the watch-type mobile terminal 200.

For instance, if a single touch or a long touch is applied to the notification message 1010 as shown in FIG. 10A(a), stress relief information generated from the mobile terminal 100 (e.g., a music icon 1020) may be output as shown in FIG. 10A(b).

As shown in FIG. 10B(a), if a single touch or a long touch is applied to a time boundary region 1001P of the watch-type mobile terminal 200 (e.g., a boundary region indicating 10:00 AM) which is out of the region of the notification message 1010, current time information (10:00 AM) is transmitted to the mobile terminal 100. Then, the mobile terminal 100 generates stress relief information, based on context information stored in an efficient recovery section and detected at a time point corresponding to the received current time information (10:00 AM). As a result, as shown in FIG. 10B(b), stress relief information (e.g., 'exercise') 1030 generated based on context information corresponding to an efficient recovery section and detected at about 10:00 AM, is popped-up on the display unit 151.

Figure 10C:
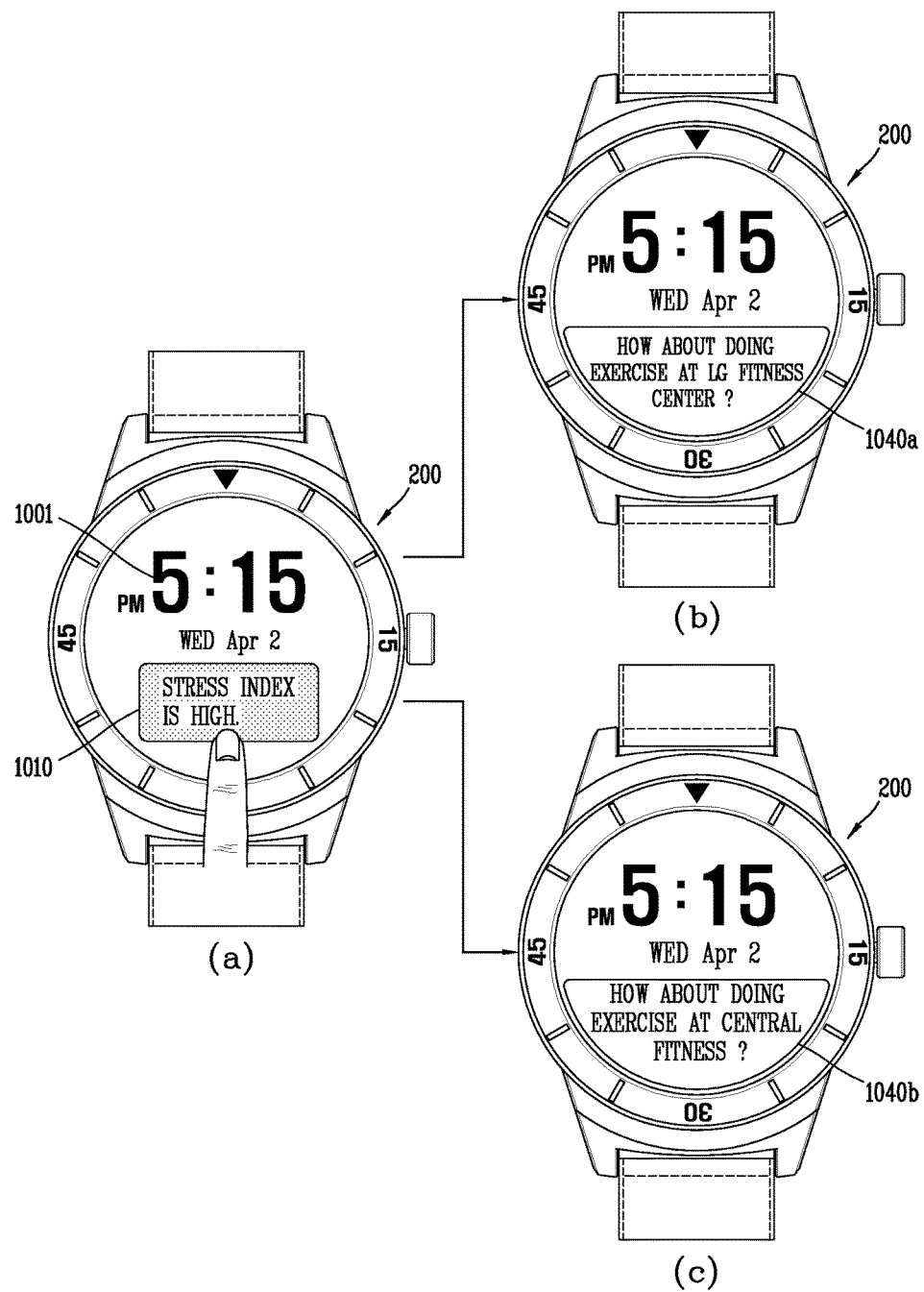

As another example, if a single touch or a long touch is applied to a notification message 1010 as shown in FIG. 10C(a), place information 1040a, 1040b related to stress relief information with respect to a current position of the watch-type mobile terminal 200 may be displayed as shown in FIGS. 10C(b) and (b"). In this case, if a touch input is applied to the place information 1040a, 1040b, a map screen or a voice guidance which guides a corresponding place may be output.

In the mobile terminal and the method for controlling the same according to the present invention, only context information generated at a section where a stress index has been efficiently decreased based on a user's biometric information, is collected to be provided to a time point when a decrease of the stress index is delayed. This may allow stress to be reduced more efficiently, and may provide a service specific to a user. Further, since context information generated at a section where a stress index has been efficiently decreased is accumulated, a stress relief pattern suitable for a user may be displayed. Further, information related to a current time and/or a user's current position is provided to induce a situation corresponding to the stress relief pattern. This may allow the user to manage stress more actively and enhance user's convenience.

Various embodiments may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal. The foregoing embodiments are merely exemplary and are not to be considered as limiting the present disclosure. The present teachings can be readily applied to other types of methods and apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

The invention claimed is:

1. A mobile terminal, comprising:
   a memory configured to store information;
   a display configured to display information; and
   a controller configured to:
   receive a user's biometric information sensed by a sensor;
   calculate a stress index based the received biometric information;
   recognize the user's stress pattern based on analyses of the stress index accumulated for a predetermined time period;
   cause the display to display notification information when increase of the stress index is detected based on the user's stress pattern;
   activate at least one sensor of the mobile terminal to collect context information;
   detect a first section where a decrease rate of the increased stress index exceeds a reference range based on the user's stress pattern;
   cause the memory to store context information collected in the first section with time information such that a plurality of context information associated with different time information is stored by storing context information repeatedly whenever the first section is detected;
   detect a second section where a decrease rate of the increased stress index is less than the reference range based on the user's stress pattern;
   cause the display to display stress relief information generated based on stored context information associated with time information corresponding to an occurrence time point of the second section or a detection time point of the second section among the plurality of context information; and
   execute a function related to the stress relief information in response to an input received in response to the stress relief information.

2. The mobile terminal of claim 1, wherein a starting point of each of the first and second sections is a time point when the increased stress index starts to be decreased, and an ending point of each of the first and second sections is a time point when the decreased stress index reaches a preset minimum value.

3. The mobile terminal of claim 2, wherein the context information is related to at least one of a position of the mobile terminal, a user's state information, a user's motion information, or surrounding environment information, at the first section.

4. The mobile terminal of claim 1, wherein the controller is further configured to cause the display to:
   display notification information at a time point when the increased stress index exceeds a reference value as a monitoring result; and
   display the generated stress relief information in response to lapse of a reference time after the notification information is displayed.

5. The mobile terminal of claim 4, wherein the stress relief information is at least one of a message which guides a stress index decreasing situation corresponding to the stored context information, an image, or a graphic change.

6. The mobile terminal of claim 4, wherein the stress relief information is displayed in a pop-up window including selection icons to select for information reception and non-reception, and
   wherein in response to an input received via a selection icon, the controller is further configured to:
   measure a time taken for the increased stress index to be relieved; and
   record the measured time together with the stored context information.

7. The mobile terminal of claim 1, wherein when a section where a decrease rate of the increased stress index is greater than the decrease rate in the first section is detected, the controller is further configured to update the context information stored in the memory.

8. The mobile terminal of claim 1, wherein when the second section occurs, the controller is further configured to generate the stress relief information by preferentially extracting context information having a larger decrease rate of the increased stress index among the plurality of stored context information.

9. The mobile terminal of claim 1, wherein the controller is further configured to:
   detect a third section where the stress index is less than a predetermined minimum value; and
   cause the memory to further store second context information corresponding to the detected third section.

10. The mobile terminal of claim 9, wherein when the stress index does not reach the predetermined minimum value within a preset time after displaying the stress relief information, the controller is further configured to:
    generate second stress relief information based on the stored second context information; and
    cause the display to display the second stress relief information.

11. The mobile terminal of claim 1, wherein in response to an input for selecting a reference time received via the display, the controller is further configured to:
    generate a stress relief pattern based on a plurality of context information accumulated for a reference time corresponding to the input; and
    cause the display to display a graphic object indicating the generated stress relief pattern.

12. The mobile terminal of claim 11, wherein the stress relief pattern is obtained by grouping same or similar context information detected for the reference time and corresponding to the first section, and wherein the graphic object is a graph showing accumulated information of the same or similar context information, on the generated stress relief pattern.

13. The mobile terminal of claim 1, further comprising a wireless communication unit configured to receive the biometric information by connecting to an external device comprising the sensor.

14. The mobile terminal of claim 13, wherein when the second section occurs, the controller is further configured to cause the wireless communication unit to transmit a notification signal indicating a delayed state of a decrease of the stress index to the external device, and
wherein in response to an input applied from the external device which has received the notification signal, the controller is further configured to control the wireless communication unit such that stress relief information generated based on the stored context information is output from the external device.

15. The mobile terminal of claim 1, wherein the reference range is a stress index decrease rate corresponding to a time taken for the user to naturally relieve increased stress without depending on an external situations.

16. The mobile terminal of claim 1, wherein the controller is further configured to ignore context information collected at a section where a decrease rate of an increased stress index is less than the reference range.

17. A method for controlling a mobile terminal, the method comprising:
receiving a user's biometric information sensed by a sensor;
calculating a stress index based on the received biometric information;
recognizing the user's stress pattern based on analyses of the stress index accumulated for a predetermined time period;
displaying notification information on a display of the mobile terminal when increase of the stress index is detected based on the user's stress pattern;
activating at least one sensor of the mobile terminal to collect context information;
detecting a first section where a decrease rate of the increased stress index exceeds a reference range based on the user's stress pattern;
storing context information collected in the first section with time information such that a plurality of context information associated with different time information is stored by storing context information repeatedly whenever the first section is detected;
detecting a second section where a decrease rate of the increased stress index is less than the reference range based on the user's stress pattern;
displaying, on the display, stress relief information generated based on the context information stored at a time corresponding to an occurrence time point of the second section or a detection time point of the second section among the plurality of context information; and
executing a function related to the stress relief information in response to an input received in response to the stress relief information.

18. The method of claim 17, further comprising:
detecting a third section where the stress index is less than a predetermined minimum value;
storing second context information corresponding to the detected third section; and
when the stress index does not reach the predetermined minimum value within a preset time after displaying the stress relief information, outputting second stress relief information generated based on the stored second context information.

* * * * *